US010493190B2

(12) United States Patent
Rudser

(10) Patent No.: US 10,493,190 B2
(45) Date of Patent: Dec. 3, 2019

(54) VAD CONTROLLER TESTER

(71) Applicant: HeartWare, Inc., Mounds View, MN (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 363 days.

(21) Appl. No.: 15/392,390

(22) Filed: Dec. 28, 2016

(65) Prior Publication Data

US 2017/0182232 A1 Jun. 29, 2017

Related U.S. Application Data

(60) Provisional application No. 62/271,624, filed on Dec. 28, 2015.

(51) Int. Cl.
*A61M 1/10* (2006.01)
*A61M 1/12* (2006.01)
*G05B 17/02* (2006.01)

(52) U.S. Cl.
CPC .......... *A61M 1/1086* (2013.01); *A61M 1/122* (2014.02); *G05B 17/02* (2013.01); *A61M 2205/18* (2013.01); *A61M 2205/3303* (2013.01); *A61M 2205/50* (2013.01); *A61M 2205/52* (2013.01); *A61M 2205/70* (2013.01)

(58) Field of Classification Search
USPC ........................................................ 600/17
See application file for complete search history.

(56) References Cited

U.S. PATENT DOCUMENTS

| 7,856,335 | B2 | 12/2010 | Morello et al. |
| 7,972,122 | B2 | 7/2011 | LaRose et al. |
| 8,007,254 | B2 | 8/2011 | LaRose et al. |
| 8,419,609 | B2 | 4/2013 | Shambaugh, Jr. et al. |
| 8,512,013 | B2 | 8/2013 | LaRose et al. |
| 8,876,850 | B1 | 11/2014 | Vollmers et al. |
| 2002/0016568 | A1* | 2/2002 | Lebel ................. A61N 1/37211 604/131 |
| 2010/0130809 | A1* | 5/2010 | Morello ............... A61M 1/1086 600/16 |
| 2010/0274218 | A1* | 10/2010 | Yodfat ................ A61M 5/1413 604/504 |

OTHER PUBLICATIONS

International Search Report and Written Opinion dated Apr. 7, 2017, for corresponding International Application No. PCT/US2016/068866; International Filing Date: Dec. 28, 2016 consisting of 18-pages.

\* cited by examiner

*Primary Examiner* — Nicole F Lavert
(74) *Attorney, Agent, or Firm* — Christopher & Weisberg, P.A.

(57) ABSTRACT

A control circuit for monitoring operation of an implantable blood pump, the control circuit operatively couplable to a testing apparatus for simulating blood pump operating conditions and testing the control circuit based on the simulated blood pump operating conditions. The control circuit includes an input module for receiving at least one of one of actual operating data from an implantable blood pump and simulated operating data from the testing apparatus. A processor for processing the received operating data is included, the processor configured to determine a source of the received operating data, and to determine whether the received operating data is actual operating data or simulated operating data based on the determined source.

11 Claims, 4 Drawing Sheets

VAD CONTROLLER TESTER

CROSS-REFERENCE TO RELATED APPLICATION

This application is related to and claims priority to U.S. Provisional Patent Application Ser. No. 62/271,624, filed Dec. 28, 2015, entitled VAD CONTROLLER TESTER, the entirety of which is incorporated herein by reference.

STATEMENT REGARDING FEDERALLY SPONSORED RESEARCH OR DEVELOPMENT n/a

TECHNICAL FIELD

The present invention relates to methods and devices for managing control circuits that monitor operation of an implantable blood pump.

BACKGROUND

An implantable blood pump used as a mechanical circulatory support device or "MCSD" includes a pumping mechanism to move blood. The pumping mechanism may be a radial flow pump, such as the HVAD® Pump manufactured by HeartWare, Inc. in Miami Lakes, Fla., USA. The HVAD® Pump is further discussed in U.S. Pat. No. 8,512,013, the disclosure of which is hereby incorporated herein in its entirety. Alternatively, the pumping mechanism may be an axial flow pump, such as the MVAD® Pump, also manufactured by HeartWare, Inc., and the pumps described in U.S. Pat. Nos. 7,972,122, 8,007,254 and 8,419,609, the disclosures of which are also hereby incorporated herein in their entirety, or any other pump suitable for providing vascular assistance. In operation, the blood pump draws blood from a source such as the left ventricle or left atrium of a patient's heart and propels the blood into an artery such as the patient's ascending aorta. Due to the nature of the application, the pumping mechanism must be highly reliable. Patient comfort is also a significant consideration. In addition to the pumping mechanism, the device may include a controller and the drive electronics for the pumping mechanism. The controller and drive electronics may receive power from an external power source. That power may be used to drive the pumping mechanism.

The control circuit may be configured to monitor operation of the blood pump. Such monitoring may be performed during power-up and afterwards. The monitoring may involve collecting data for measuring, estimating, calculating or otherwise determining operational parameters of the pump (e.g., motor speed), operational parameters of the control circuit (e.g., mode of operation, power supplied to the motor), and/or physiological parameters of the patient (e.g., heart rate, blood flow rate). During such monitoring, if the control circuit detects an unwanted condition, such as an error in the operation of the pump, an error in the operation of the control circuit, the presence of an undesirable condition at the blood pump (e.g., a suction condition, high blood pressure condition), or the presence of an undesirable physiological condition of the patient (e.g., arrhythmia, thrombosis, cardiovascular accident), the control circuit may take action to address the undesirable condition, such as by providing an alert to the patient or to a clinician, or by control operation of a motor of the pump to attempt to clear or mitigate the undesirable condition. In some cases, the control circuit may be capable of predicting an upcoming or future undesirable condition based on the collected data.

The control circuit may further keep a log of the collected data. The logged data may be stored for later analysis, such as clinical interpretation of long-term changes or features in the collected data. For instance, lifestyle information about the patient (e.g., when the patient is more or less active) may be determined from blood flow estimations. For further example, a patient's risk of cardiovascular accident may be predicted using months to years of collected data from a control circuit, for instance, in the manners described in commonly owned and U.S. Provisional Application Ser. No. 62/249,601, the disclosure of which is hereby incorporated herein in its entirety.

SUMMARY

The present invention advantageously provides a control circuit for monitoring operation of an implantable blood pump, the control circuit operatively couplable to a testing apparatus for simulating blood pump operating conditions and testing the control circuit based on the simulated blood pump operating conditions. The control circuit includes an input module for receiving at least one of actual operating data from an implantable blood pump and simulated operating data from the testing apparatus. A processor for processing the received operating data is included, the processor configured to determine a source of the received operating data, and to determine whether the received operating data is actual operating data or simulated operating data based on the determined source.

In another aspect of this embodiment, the processor is communicatively couplable to a data store and further configured to log, in the data store, the received operating data and an indication of whether the received operating data is simulated operating data.

In another aspect of this embodiment, the processor is configured to log the actual operating data in a data log, and to omit the simulated operating data from the data log containing the actual operating data.

In another aspect of this embodiment, the processor is further configured to detect an adverse physiological event based on the received operating data, to provide an alert in response to detection of the adverse physiological event, and to override providing the alert in response to determining that the received operating data is simulated operating data.

In another aspect of this embodiment, the adverse physiological event is at least one from the group consisting of a ventricular suction condition, a high blood pressure condition, an arrhythmia, thrombosis, and a stroke.

In another aspect of this embodiment, the processor is further configured to detect an operational pump error based on the received operating data, to provide an alert in response to detection of the operational pump error, and to override providing the alert in response to determining that the received operating data is simulated operating data.

In another aspect of this embodiment, the operational pump error is at least one from the group consisting of a sudden change in pump speed and a change in hematocrit level.

In another aspect of this embodiment, the control circuit is communicatively coupled to a hospital alarm system, and wherein the processor is further configured to transmit the alert through a communications link to the hospital alarm system, and to override transmitting the alert in response to determining that the received operating data is simulated operating data.

In another embodiment, a method of managing data indicating an operation of an implantable blood pump includes at a control circuit, receiving data indicative of at least from the group consisting of physiological activity and operational activity at an implantable blood pump, the data being at least from the group consisting of (i) actual operating data from an implantable blood pump coupled to the control circuit and (ii) simulated operating data from a testing apparatus coupled to the control circuit. At the control circuit, determining whether the received data is from a testing apparatus. At the control circuit, controlling an activity of the control circuit based on a determination that the received data is from a testing apparatus.

In another aspect of this embodiment, the method further includes storing the received data in a memory and when the received data is determined to be from a testing apparatus, storing an indication of the determination in the memory and classifying the received data as simulated operating data.

In another aspect of this embodiment, the method further includes storing the actual operating data in a data log and omitting the simulated operating data from the data log containing the actual operating data.

In another aspect of this embodiment, controlling an activity of the control circuit includes sending an alert.

In another aspect of this embodiment, controlling an activity of the control circuit includes overriding the alert, the alert responsive to detection of an adverse physiological event based on the received operating data.

In another aspect of this embodiment, the adverse physiological event is at least one from the group consisting of a ventricular suction condition, high blood pressure condition, an arrhythmia, thrombosis, and a stroke.

In another aspect of this embodiment, controlling an activity of the control circuit includes overriding the alert, the alert responsive to detection of an operational pump error based on the received operating data.

In another aspect of this embodiment, the adverse physiological event is at least one from the group consisting of a sudden change in pump speed and a change in hematocrit level.

In another aspect of this embodiment, overriding the alert includes overriding transmission of the alert to a hospital alarm system.

In yet another embodiment, an apparatus for testing operation of a control circuit, the control circuit configured to monitor operation of an implantable blood pump, the apparatus operatively couplable to the control circuit and includes a memory for storing instructions for simulating operation of the implantable blood pump. A processor configured to generate simulated operational data of the implantable blood pump based on the stored instructions is included. A communication interface for transmitting to the control circuit the simulated operational data and an indication that the operation data is simulated is included.

In another aspect of this embodiment, the control circuit includes a data log, and wherein the indication is formatted for inclusion with the simulated operation data in the data log.

In another aspect of this embodiment, the apparatus is adapted to receive from the control circuit, through the communication interface, a test result, and wherein the processor is configured to provide the test result to a display device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
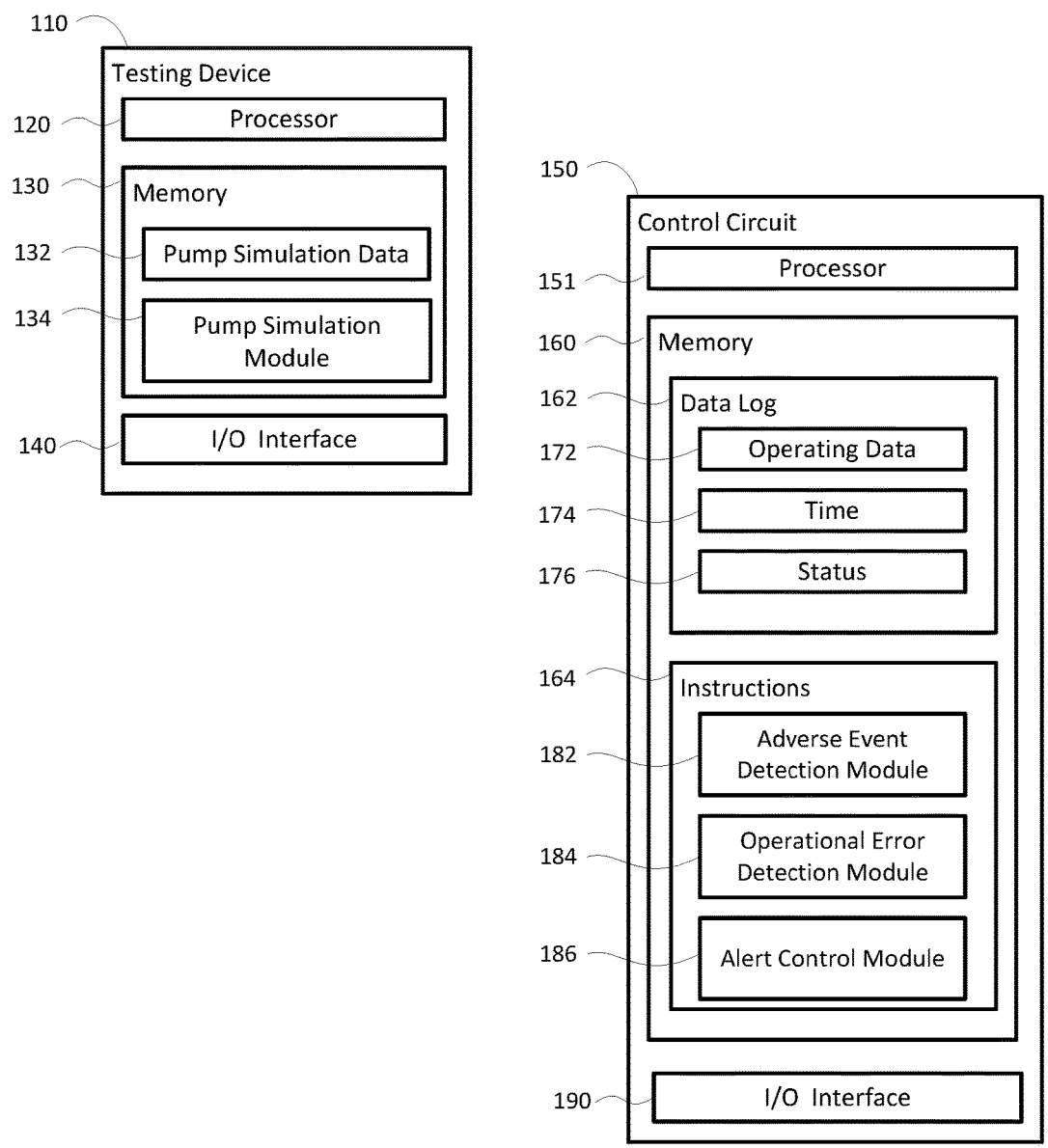
FIG. 1 is a block diagram of an example system having a testing device and control circuit in accordance with an aspect of the disclosure.

In order to ensure proper operation of the control circuit, the present disclosure provides for a testing device that may be connected to the control circuit. The testing device may generate data simulating operation a blood pump, sensor, or other device connected to the control circuit (e.g., a battery). The simulated data may simulate various conditions and/or operating modes of the device (e.g., normal operation, suction condition of a pump, low battery condition of a battery, etc.). The control circuit may then monitor the simulated data.

Because it is predetermined what condition is being simulated by the testing device, it may be easily determined whether the control circuit identifies the condition correctly. If the condition simulated by the collected data is correctly identified, and the control circuit takes appropriate responsive action (or, for instance during normal operation, no action), then it may be determined that the control circuit is operating correctly. If the condition is not correctly identified, e.g., the control circuit identifies a false positive or false negative, or if the control circuit responds to a particular determination incorrectly, then the control circuit may be reprogrammed other calibrated to operate correctly.

Testing a control circuit can have undesirable effects. For instance, when responding to the simulated data, the control circuit may sound an alert or otherwise summon a doctor or clinician to provide immediate medical assistance to a patient of a device assumed to be controlled by the control circuit. While those individuals operating the testing device may be aware that the alert is only in response to a simulation, and is not a real emergency, the doctor or clinician who is alerted by the control circuit may themselves be unaware, and thus may be needlessly inconvenienced to respond to the alert.

For further instance, the simulated data may be logged along with the other collected data. However, the simulated data is merely a simulation, and not indicative of actual parameters of the connected devices or of the patient. In this regard, if a clinician or the control circuit were to attempt to analyze the logged data, the simulated data included therein may corrupt that analysis.

The present disclosure further provides for a testing device capable of generating simulated data related to operation of an implantable blood pump, providing the generated data to a control circuit in order to test functionality of the control circuit, and further providing an indication to the control circuit that the provided data is simulated data (as compared to actual data from a blood pump). The present disclosure also provides for a control circuit capable of responding differently to the received data depending on whether the control circuit receives an indication that the data is simulated data (or alternatively, receives an indication that the data is actual data from a blood pump). The present disclosure further provides for a system including the above testing device and control circuit, as well as methods of operation for each of the testing device and control circuit.

Referring now to the drawings in which like reference designators refer to like elements, there is shown in FIG. 1 an exemplary system 100 having a testing device 110 and control circuit 150. Each of the testing device 110 and the control circuit 150 includes a respective interface 140, 190 over which data and/or instructions may be sent/received, at least from the testing device 110 to the control circuit 150, but optionally also bi-directionally. Each of the testing device 110 and the control circuit 150 also includes a respective processor 120, 151, such as a general-purpose processor, and memory 130, 160. Each processor 120, 151 may be any well-known processor, such as commercially available processors. Alternatively, the processor may be a dedicated controller such as an ASIC. Each memory 130, 160 stores information accessible by its respective processor 120, 151, including instructions that may be executed by the processor. Each memory also includes data that may be retrieved, manipulated or stored by the processor 120, 151. The memory 130, 160 may be of any type capable of storing information accessible by the processor, such as a hard-drive, memory card, ROM, RAM, DVD, CD-ROM, write-capable, and read-only memories.

Although FIG. 1 functionally illustrates the processors and memories as being within the same device/circuit block, it will be understood that the processor and memory for each of the testing device and control circuit may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

With regard to the memory 130 of testing device 110, the memory may store data including pump simulation data 132 and instructions (e.g., pump simulation module 134) for executing the pump simulation data 132. The pump simulation data 132 may be any information related to operation of a blood pump, including operational parameters of the pump (e.g., motor speed, rotor position, back-EMF voltages, operating current, etc.) as well as any additional parameters that may be derived from the operational parameters (e.g., estimated blood flow, estimated pump differential pressure, etc.). The pump simulation data 132 may include physiological parameters of a patient using the pump (e.g., heart rate, blood pressure, etc.). The pump simulation data 132 may include operating parameters (e.g., power received, temperature, etc.) of control circuitry associated with an implantable pump (e.g., backup battery, implanted electronics, transcutaneous energy transfer apparatus, etc.).

The pump simulation module 134 may be capable of producing data signals simulating a predetermined condition. Predetermined conditions may include normal operation of a pump and its associated electronics. Predetermined conditions may also include undesirable conditions, such as a ventricular suction condition at the pump (or onset thereof), a low flow condition at the pump, pump slowdown, pump stoppage, a overheating of the associated electronics, or data indicative of an adverse physiological condition. Adverse conditions may include inherently adverse conditions (e.g., arrhythmia, thrombosis, stroke, other cardiovascular accident, etc.) as well as sudden changes of physiological conditions that may indirectly cause an adverse condition (e.g., a sudden change of pump speed indicative of an increased risk of inflow occlusion or hypertensive condition, changes in hematocrit, etc.). The predetermined conditions generated by the pump simulation module 134 may be used to test control circuits to ensure that the control circuits accurately identify and correctly respond to those conditions as they occur (e.g., signals representing those conditions are received). The memory 160 of the control circuit 150 may include a data log 162 for storing received operating data 172, e.g., pump simulation data. The control circuit 150 may further log a respective time 174 that given data is received.

Figure 2:
FIG. 2 is an example data log of a control circuit in accordance with an aspect of the disclosure.

In some examples, the data log 162 may also store a status 176 of the received operating data, for instance, whether the data is simulated data from a testing device or actual data gathered from a blood pump or associated apparatus. FIG. 2 shows an example log 200 showing data indicating (in the left column) a flow rate of blood at the pump, and for each flow rate reading (which may be an estimation based on, for example, pump speed, BEMF, and/or current supply readings), there is a corresponding entry (in the right column) indicating whether or not the left column reading is received from or based on simulated data ("Test") or not (blank). In other examples, the control circuit 150 may be capable of omitting simulated data from the data log 162, or storing the simulated data in a separate data log 162. In such examples, the data log 162 may not need to store a status 176 of the received data, since it may be assumed that all data included in the log is received from an actual implantable device, and not from a testing device.

The memory of the control circuit 150 may further include various instructions or modules 164 for executing operations based on the received data. For example, the control circuit 150 may include an adverse event detection module 182 for detecting an undesirable physiological condition based on the received data. For further example, the control circuit 150 may include an operation error detection module 184, which may detect an undesirable condition in the blood pump (e.g., suction condition) or at associated electronics (e.g., overheating condition). The control circuit 150 may further include an alert control module 186 for responding to detected adverse events and/or operational errors. Such responses may involve providing an alert to the patient, or to a clinician. In a hospital or other clinical setting, the alert control module may be operable to provide the alert over a hospital emergency system (or similarly clinic emergency system) to indicate a need for immediate assistance.

The processor 151 of the control circuit 150 may be further operable to determine a source of the received data, thereby determining whether the received data is actual or simulated data. The source of the data may be inferred from the received operation data itself (e.g., including an indication of a source in the data), or based on a separate signal indicating a particular device that is connected to the control circuit. The separate signal could be a manual switch which would be thrown when the control circuit is connected to the testing device. The separate signal could alternatively be a pin on the interface of the control circuit, which could be shorted to ground when one of the testing device or an implantable device is connected, and shorted to power when the other is connected. Alternatively, the testing device and implantable device could connect to the control circuit through entirely different ports, such that a connection to a particular port of the control circuit would indicate the type of device that is connected.

The example system described above may be operated using the methods described herein. It should be understood that the following operations do not have to be performed in the precise order described below. Rather, various operations can be handled in a different order or simultaneously. It should also be understood that these operations do not have to be performed all at once. For instance, some operations may be performed separately from other operations. Moreover, operations may be added or omitted.

Figure 3:
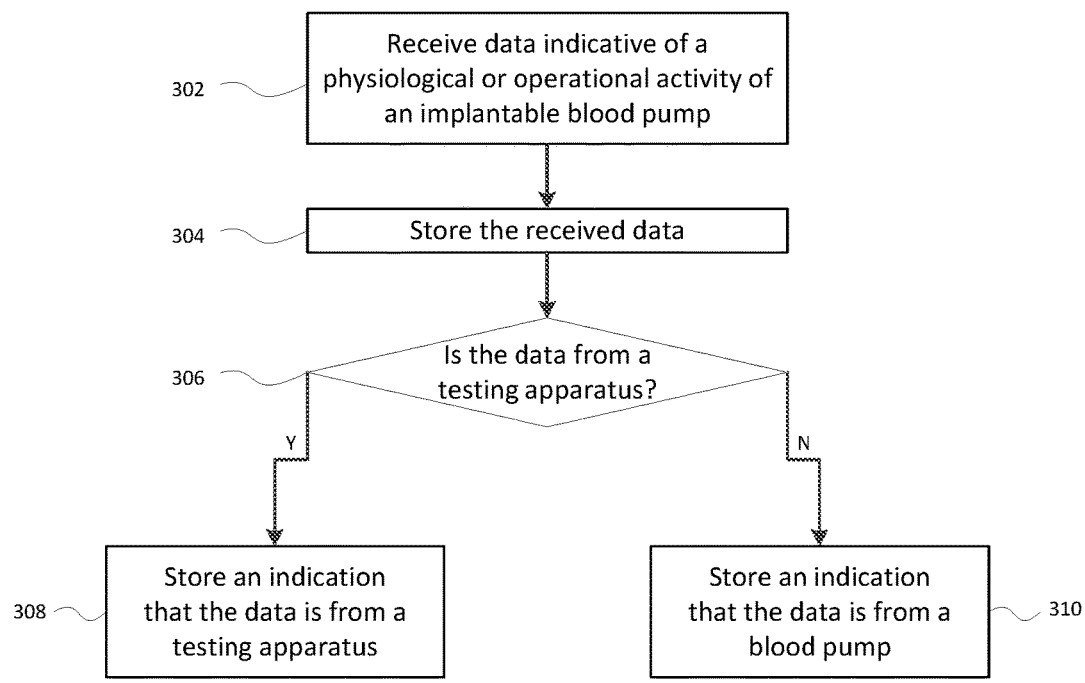
FIG. 3 is a flow diagram of an example method of managing data indicating an operation of an implantable blood pump, in accordance with various aspects of the disclosure.

Referring now to FIG. 3, the storage may take place at a memory or other data store of, or remote from, the control circuit. For example, data logs may be used to analyze patient health, analyze long-term pump operation, develop new methods for diagnosing or predicting health risks, and/or improve pump technology. However, if the data log includes information that is merely reflective of simulated data and not actual pump operation, the usefulness of the log for the above purposes may be compromised, thereby corrupting the data. Storing an indication of whether the received data is actual or simulated data is beneficial for preventing such corruption of the stored data. For instance, in the example of FIG. 2, it is clear from the status column of the data log which data entries are actual data (and thus useful for further analysis and development) and which data is simulated data (and thus not useful).

At 302, the control circuit 150 receives data indicative of a physiological or operational activity of an implantable blood pump or associated circuitry. At 304, the control circuit 150 stored the received data. At 306, the control circuit 150 determines whether or not the data is provided from a testing device. This determination may be made based on whether at least some of the received data includes a signal indicating that the data was provided from a testing device. If the received data is determined to have been provided from a testing device, then at 308 an indication of that data source may be stored with the rest of the received data. If the received data is not determined to have been provided from a testing device, then at 301, the control circuit 150 may determine not to store any such indication with the received stored data. Alternatively, an indication may be provided for received data provided from a testing device, but not for other received data. In other examples, if the received data is determined to have been provided from a testing device, then the control circuit 150 may determine not to store the received data at all, or to store it in a separate log file.

Figure 4:
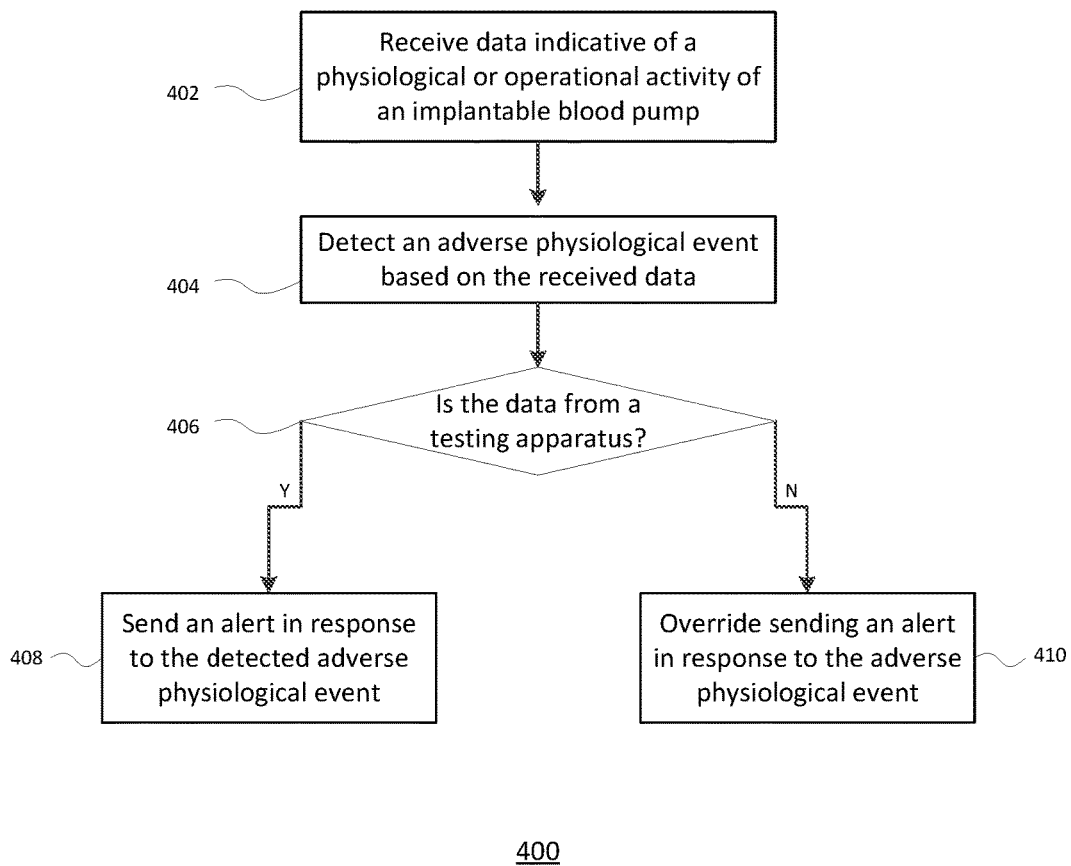
FIG. 4 is another diagram of an example method of managing data indicating an operation of an implantable blood pump, in accordance with various aspects of the disclosure.

Now referring to FIG. 4, as explained above, the purpose of the simulation data from the testing device is to ensure that the control circuit 150 interprets the simulation data correctly and responds to the data appropriately. However, as mentioned above, it may inconvenience some individuals if the control circuit 150 issues an alert without indicating that the alert is only a test. By providing an indication of whether the received data is actual or simulated data, the control circuit 150 may determine between issuing an actual alert, or issuing a test alert (or simply overriding sending an actual alert). At 402, the control circuit 150 receives data indicative of a physiological or operational activity of an implantable blood pump. At 404, the control circuit 150 detects an unwanted condition (e.g., adverse physiological event, operational error, etc.) based on the received data. At 406, it is determined whether the data from which the condition detected at 404 is actual data (e.g., from an actual pump or associated circuitry) or simulated data (e.g., from a testing device). If the data is determined to be actual data, then at 408, the control circuit 150 issues an alert in response to having detected the unwanted condition. If the data is determined to be simulated data, then at 401, the control circuit 150 overrides sending the alert of 408.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A control circuit for monitoring operation of an implantable blood pump, the control circuit operatively couplable to a discrete testing apparatus configured to simulate blood pump operating conditions and testing the control circuit based on the simulated blood pump operating conditions, the control circuit comprising:
   an input module for receiving at least one from the group consisting of actual operating data from the implantable blood pump and simulated operating data from the testing apparatus;
   a processor for processing the received operating data, the processor configured to determine a source of the received operating data, and to determine whether the received operating data is one from the group consisting actual operating data from the implantable blood pump and simulated operating data based on the determined source.

2. The control circuit of claim 1, wherein the processor is communicatively couplable to a data store and further configured to log, in the data store, the received operating data and an indication of whether the received operating data is simulated operating data.

3. The control circuit of claim 1, wherein the processor is configured to log the actual operating data in a data log, and to omit the simulated operating data from the data log containing the actual operating data.

4. The control circuit of claim 1, wherein the processor is further configured to detect an adverse physiological event based on the received operating data, to provide an alert in response to detection of the adverse physiological event, and to override providing the alert in response to determining that the received operating data is simulated operating data.

5. The control circuit of claim 4, wherein the adverse physiological event is at least one from the group consisting of a ventricular suction condition, a high blood pressure condition, an arrhythmia, thrombosis, and a stroke.

6. The control circuit of claim 1, wherein the processor is further configured to detect an operational pump error based on the received operating data, to provide an alert in response to detection of the operational pump error, and to override providing the alert in response to determining that the received operating data is simulated operating data.

7. The control circuit of claim 6, wherein the operational pump error is at least one from the group consisting of a sudden change in pump speed and a change in hematocrit level.

8. A method of managing data indicating an operation of an implantable blood pump, comprising:
   at a control circuit, receiving data indicative of at least one from the group consisting of physiological activity and operational activity at an implantable blood pump, the data being at least from the group consisting of (i) actual operating data from the implantable blood pump coupled to the control circuit and (ii) simulated operating data from a discrete testing apparatus coupled to the control circuit;

at the control circuit, determining whether the received data is from the testing apparatus; and at the control circuit, controlling an activity of the control circuit based on a determination that the received data is from the testing apparatus.

9. The method of claim 8, wherein the method further includes:

storing the received data in a memory; and when the received data is determined to be from a testing apparatus, storing an indication of the determination in the memory and classifying the received data as simulated operating data.

10. The method of claim 8, further comprising:

storing the actual operating data in a data log; and omitting the simulated operating data from the data log containing the actual operating data.

11. An apparatus for testing operation of a control circuit, the control circuit configured to monitor operation of an implantable blood pump, the apparatus operatively couplable to the control circuit and discrete from the control circuit and the implantable blood pump, the apparatus comprising:

a memory for storing instructions for simulating operation of the implantable blood pump;

a processor configured to generate simulated operational data of the implantable blood pump based on the stored instructions; and a communication interface for transmitting to the control circuit the simulated operational data and an indication that the operation data is simulated.

* * * * *